United States Patent [19]

Strickland et al.

[11] Patent Number: 5,191,899
[45] Date of Patent: Mar. 9, 1993

[54] PAP SMEAR COLLECTION DEVICE WITH BRISTLES ORIENTED IN A PLANE

[75] Inventors: Richard D. Strickland, Sandy, Utah; Geno Saccomanno, Grand Junction, Colo.

[73] Assignee: Baal Associates, Inc., Sandy, Utah

[21] Appl. No.: 806,583

[22] Filed: Dec. 12, 1991

[51] Int. Cl.⁵ ............................................. A61B 10/00
[52] U.S. Cl. ...................................... 128/756; 128/759
[58] Field of Search ............... 128/749, 756, 757, 759, 128/778; 15/159 A; 606/161

[56] References Cited

U.S. PATENT DOCUMENTS

| | | | |
|---|---|---|---|
| Re. 27,915 | 2/1974 | Kohl | 128/757 |
| 3,485,236 | 12/1969 | Frost | 128/757 |
| 3,613,664 | 10/1971 | Willson | 128/756 |
| 3,633,565 | 1/1972 | McDonald | 128/2 R |
| 3,774,590 | 11/1973 | McDonald | 128/2 B |
| 3,881,464 | 5/1975 | Levene | 128/2 B |
| 4,078,656 | 3/1978 | Crane et al. | 206/223 |
| 4,127,113 | 11/1978 | Nollan | 128/2 W |
| 4,384,587 | 5/1983 | Milgrom | 128/757 |
| 4,700,713 | 10/1987 | Kist | 128/756 |
| 4,754,764 | 7/1988 | Bayne | 128/756 |
| 4,759,376 | 7/1988 | Stormby | 128/756 |
| 4,762,133 | 8/1988 | Bayne et al. | 128/756 |
| 4,873,992 | 10/1989 | Bayne | 128/756 |
| 4,981,143 | 1/1991 | Sakita et al. | 128/757 |
| 5,022,408 | 6/1991 | Mohajer | 128/756 |

FOREIGN PATENT DOCUMENTS

| | | | |
|---|---|---|---|
| 653880 | 1/1986 | Switzerland | 128/757 |
| 2204496 | 11/1988 | United Kingdom | 128/757 |

*Primary Examiner*—Max Hindenburg
*Assistant Examiner*—Guy V. Tucker
*Attorney, Agent, or Firm*—Workman, Nydegger & Jensen

[57] ABSTRACT

A device for simultaneous collection of cells from the endocervical canal and the cervical face of the uterus and methods of use. The device is an elongated handle having one cell-collecting member projecting from the handle at an axis perpendicular to the axis of the handle for contacting with the cervical face of the uterus, and one cell-collecting member projecting from the handle along the same axis as the handle for contacting with the endocervical canal of the uterus. Along each member project sets of bristles which, because they are perpendicularly positioned on each member, provide mild abrasive action to the endocervical canal and the cervical face when the device is inserted into the uterus and rotated, so that cells from both regions are collected onto the bristles.

The cells are removed from the bristles either by bending a flexible portion of the handle to enable parallel smearing of the cells onto a microscope slide, or by dislodging the cells from the bristles of the device into a fixative solution by manually rotating the device. After the solution is centrifuged, the cells form a cell pellet which is then smeared onto a microscope slide as a single layer of cells.

36 Claims, 6 Drawing Sheets

PAP SMEAR COLLECTION DEVICE WITH BRISTLES ORIENTED IN A PLANE

BACKGROUND

1. The Field of the Invention

The present invention relates generally to apparatus and methods for use in the collection of a Pap smear. More particularly, the present invention provides a novel design which permits simultaneous collection of cells from the cervical face and from the endocervical canal. The device also provides a method and means for securing a vaginal sample without reverting to a second sampling device.

2. The Background of the Invention

Over the last 40 years, the death rate from cervical cancer has dropped dramatically due to the widespread use of the Papanicolaou ("Pap") test. This test involves the collection of cells from the cervical face, the endocervical canal and occasionally from the vaginal wall. These cells are then microscopically examined for evidence of precancerous or cancerous growth. The periodic use of this test permits early detection of malignancy so that palliative therapy can be initiated at a time when it will yield the highest possible success rate.

For many years the standard method for collection of these cells has been a wooden or plastic spatula. A variety of slightly different shapes have been used in an effort to allow the clinician to collect cells from the cervical face as well as the endocervical canal. In some cases, the opposite end of the spatula was designed to collect a vaginal scraping.

For the most part, these designs have been able to retrieve cells from the surface of the cervix and the vaginal wall but have frequently failed to collect adequate cell samples from the endocervical canal. This has been a serious problem because any sample which does not include endocervical cells is deemed to be inadequate for proper interpretation and diagnosis. Further, many women who have had an inadequate sample taken are reluctant to have the procedure repeated and may be placed at risk for progression of their disease until their next periodic checkup.

A delay in the diagnosis of cervical or uterine cancer can result in the need for far more radical treatment procedures than would be needed if the cancer were detected earlier. In the worst case, a delay in diagnosis could result in the progression from treatable cancer to a terminal cancer.

Recent modifications in collection procedures have added a cotton swab to the technique in an effort to collect endocervical cells. The cotton swab is inserted into the cervical canal and rotated. Although the cotton swab may somewhat improve the yield, it is not abrasive enough to scrape the endocervical canal and consistently retrieve an adequate sample.

Another modification made in an attempt to collect endocervical cells is what is called a "cytology brush." This cytology brush has on the end of a long handle a conically-tapering brush made of spiraling bristles. When the brush is rotated within the endocervical canal, cells become entrapped by the brush. However, while the cytology brush can consistently obtain endocervical cells, the brush is too abrasive, and so its use increases the incidence of bleeding and discomfort and, in addition, adds considerable cost to a very price-sensitive procedure.

If bleeding occurs during collection, the red blood cells may obscure other cells on the cytology slide and make interpretation difficult or impossible. When this happens, the cell collection procedure must be repeated. As many "Pap smears" are performed in public health clinics and similar free or low-cost environments, the device to be used must not substantially increase the material costs of the procedure.

Another disadvantage to the cytology brush has been that entry of the brush into the endocervical canal is difficult to control. If the brush is extended too far inside the canal, injury to the endocervix may result. It is difficult for the user to determine proper penetration of the cytology brush.

Recently, some changes in the design of cytology brushes have been taking place, aimed primarily at decreasing the incidence of cervical bleeding and improving the ease with which cells are extracted from the bristles. These changes have been somewhat effective but have typically further increased the cost of the brushes.

One change has been to design a broom-like device to simultaneously collect cells from the ectocervix and endocervix. This brush has bristles which extend forward from a cross piece and looks very much like a broom. The central bristles are longer than the lateral bristles and are intended to enter the endocervical canal while the lateral bristles make contact with the ectocervix. The collection difficulties arise from the fact that the central bristles are parallel to the walls of the endocervical canal and, thus, very little abrasive effect is generated, especially if there is any dilation of the canal. As a result, endocervical cells are not consistently collected.

Further disadvantages of the prior art devices are in transferring the cells for examination. After cells have been collected, they are usually transferred to a microscopic slide for later examination. This is accomplished by wiping the collecting apparatus, whether spatula, brush swab, or broom, directly against the surface of the slide. A fixative is then applied to avoid any deterioration of the cells before the cytology technician and/or pathologist can examine them. Unfortunately, many doctors lack time and patience to transfer every collected cell from the device with a microscopic slide and so valuable diagnostic material may be lost, resulting in risk of erroneous diagnosis. With the spiral brush, it is and excess time and care to do so is necessary. In some cases, the presence of mucous or blood or the knowledge that the patient is at high risk, can make this type of slide preparation inadequate. A monocellular preparation may be requested. In this technique, the samples must be transferred from the collection device(s) into a container of fixative. The container is then centrifuged until all cellular components have collected at the bottom of the container as a "cell pellet." After the excess fixative is pipetted off, the cell pellet can be spread evenly onto a slide. This provides a slide with very little cellular overlap. Mucous will have gone into solution and any red blood cells will be sufficiently spread so as to avoid obscuring other cells.

BRIEF SUMMARY AND OBJECTS OF THE INVENTION

In view of the present state of the art, it is an object of the present invention to provide apparatus and methods for the simultaneous collection of cells from the ectocervix and the endocervix while avoiding in the process any excess bleeding or significant increases in procedure costs.

It is another object of the present invention to provide apparatus and methods for obtaining an adequate vaginal sample using the same device as is used for simultaneous collection of cells from the ectocervix and the endocervix.

It is a further object of the present invention to provide apparatus and methods which facilitate removal of cellular components from the collection areas of the device onto a microscopic slide.

It is yet a further object of the present invention to provide apparatus and methods which facilitate the removal of cellular components from the collection areas of the device into appropriate containers for performance of a monocellular preparation.

It is yet another object of the present invention to provide apparatus and methods which reduce the potential for endocervical and cervical trauma by mechanically controlling the maximum depth of penetration of the device into the endocervix of the uterus, by conforming to the cervical face and by maintaining alignment with the endocervical canal.

A still further object of the present invention is to provide apparatus and methods to maximize the collection of cells from the endocervical canal even when said canal is dilated.

An additional object of the present invention is to provide apparatus and methods to collect cells from the ectocervix, endocervix, and vagina that are relatively inexpensive and can be used widely.

Additional objects and advantages of the invention will be set forth in the description which follows, and in part will be obvious from the description, or may be learned from the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention is directed to an apparatus and methods of use which permit simultaneous contact and collection of cells from the ectocervix and endocervix. Accordingly, the device is provided with an elongated handle having a forward end and a rear end. The forward end narrows slightly into a flexible zone which is important in the removal of cells from the device onto a microscope slide. This zone allows the handle to flex and bring the collection areas into a position parallel to the slide, thereby facilitating the transfer of cellular material onto the microscopic slide by a direct smear technique.

A member longitudinally extends from the flexible zone of the handle, along the same axis as the handle. This member is sized for comfortable insertion into the endocervical canal. Substantially perpendicularly projecting from the longitudinally extending member is a first set of bristles. Due to their being substantially perpendicular to the axis of the endocervical canal and of sufficient combined length to span the diameter of the canal, these bristles allow mildly abrasive contact with the walls of the endocervical canal even when the canal is dilated. When the canal is not dilated, these bristles are sufficiently supple to be easily compressed when entering the non-dilated cervix so as to not cause undue trauma to the endocervical walls.

A second member laterally extends from the flexible zone of the handle generally on opposite sides of the flexible zone from the same point where the longitudinally extending member extends from the flexible zone, and is positioned along an axis substantially perpendicular to the handle of the device. Projecting forwardly from the laterally extending member is a second set of bristles.

When the device is inserted into the uterus, the longitudinally extending member becomes inserted into the endocervical canal and the first set of bristles makes contact with the endocervical walls. Simultaneously, the laterally extending member is pressed against the cervical face with sufficient forward pressure to flex the second set of bristles slightly.

To reduce the potential for sampling trauma of the endocervical canal from excessive penetration of the longitudinally extending member, the laterally extending member will act as a mechanical barrier. The device can only penetrate up to the point where the laterally extending member presses against the cervical face. It will also provide a means for maintaining an axial relationship between the device and the endocervical canal, thereby preventing unwanted damage to the walls of the canal by an off-axis insertion. The laterally extending member may be curved so as to conform to the shape of the cervical face.

Once the device is comfortably placed within the uterus, the device is then rotated 360 degrees. Endocervical cells and cells from the cervical face are simultaneously collected onto the bristles of the device.

Removal of the cells from the collection device of the present invention may be accomplished by two methods. The first method is by utilizing the flexible zone of the handle to smear the cells easily onto a microscope slide with a minimum of cellular material loss. Once a fixative is applied, the cells are ready to be analyzed.

The second method is by inserting the forward end of the device into a centrifuge tube filled with a fixative solution and spinning the device between the palms of two hands. The laterally extending member is designed such that when the device is manually rotated, an oscillating turbulence, similar to that found in a washing machine, is created which effectively releases the collected cells from the set of bristles and simultaneously dissolves any collected mucous into suspension. The solution is centrifuged and a cell pellet is produced. When this pellet is spread onto a slide, a single layer of cells is available for analysis.

In one embodiment of the device, at the rear end of the handle, the handle may flatten into an elliptically-shaped spatula which may be used to perform vaginal scrapings when necessary.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention in its presently understood best mode will be described with additional specificity and detail through the use of the accompanying drawings in which.

In the drawing figures, like parts have been designated with like numerals throughout.

DETAILED DESCRIPTION OF THE PREFERRED EMBODIMENTS

Figure 1:
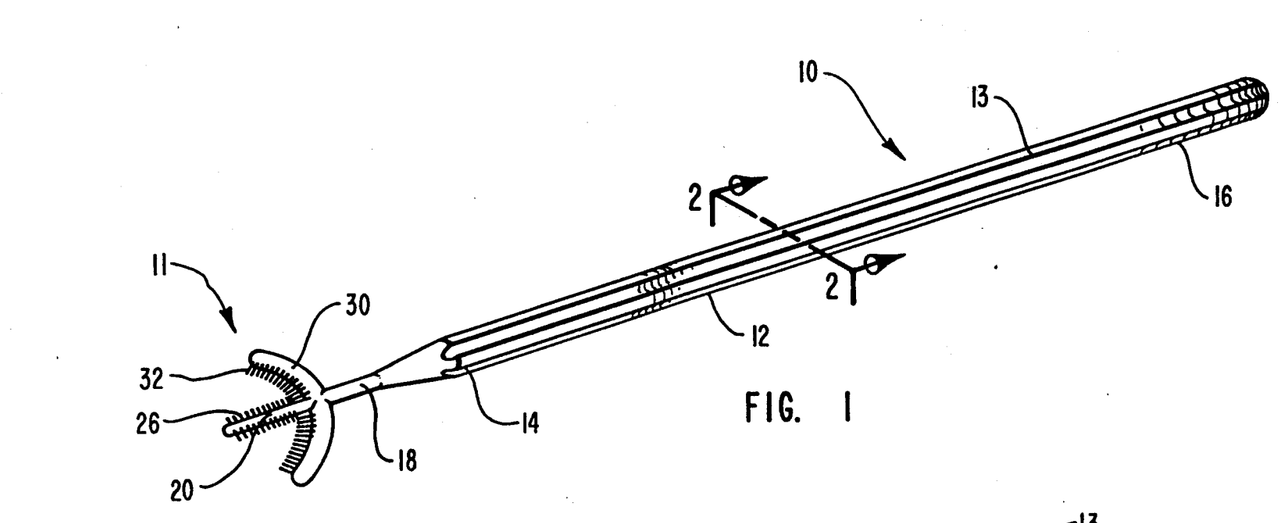
FIG. 1 is a perspective view of one embodiment of the present invention.
Figure 2:
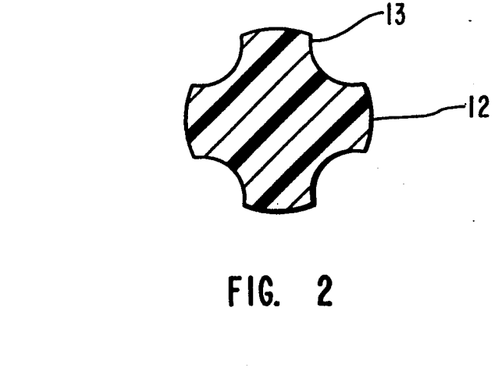
FIG. 2 is a cross-section taken along the line 2—2 of FIG. 1, illustrating the ridged shape of the handle.
Figure 3:
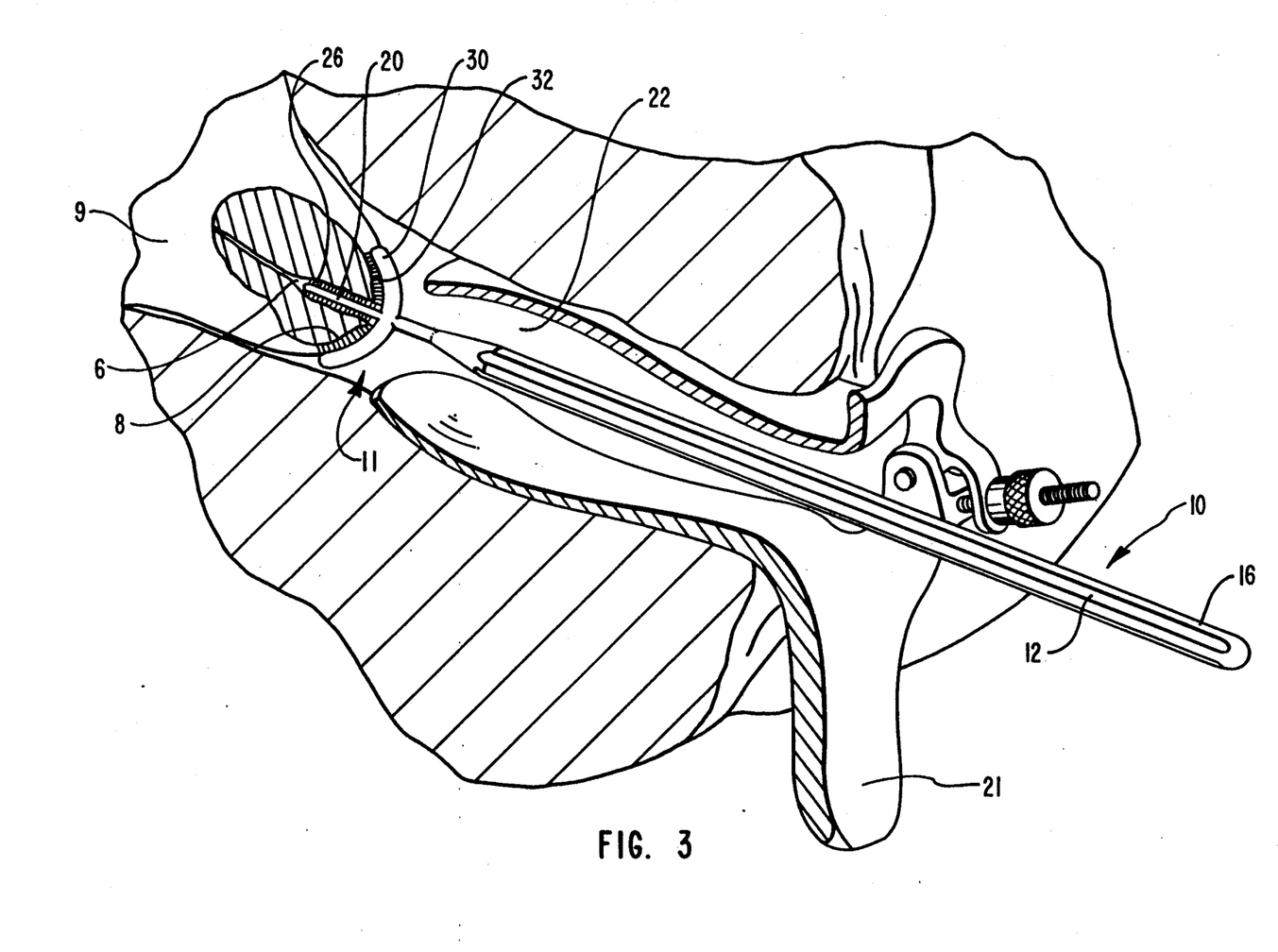
FIG. 3 is a cross-sectional view of the device of the present invention being inserted into the endocervical canal of the uterus.

Reference is first made to FIGS. 1-3 which illustrate one presently preferred embodiment of the invention and its use. The device for simultaneously contacting and collecting cells from the endocervical canal 6 and the cervical face 8 of the uterus 9 is generally designated at 10 and can be seen in use in FIG. 3. The device 10 is comprised of an elongated handle 12 and a tissue sampling means 11 for collecting cells. Although it can be appreciated that the handle 12 could be of a variety of lengths, the presently preferred length is about six inches. Handle 12 comprises longitudinally extending ridges 13 along the length of handle 12. These ridges 13 serve to provide better grip and ease of handling of the device 10. The ridges 13 provide more of a non-slip surface than would a smooth handle on the same device A cross-section of the handle 12 illustrating the longitudinally extending ridges 13 can be clearly seen in FIG. 2.

Handle 12 further comprises a forward end 14 and a rear end 16. Forward end 14 narrows into a flexible zone 18 of the handle 12. As will be seen later, flexible zone 18 is important in the deposit of cells onto microscope slides for analysis.

Tissue sampling means 11 comprises a first bristle means and a second bristle means. In the preferred embodiment within the scope of the present invention, the first bristle means comprises a member 20 which longitudinally extends from the flexible zone 18 along the same axis as the axis of the handle 12. As can be seen in FIG. 3, when the device 10 is inserted into the uterus 9, the longitudinally extending member 20 becomes inserted into the endocervical canal 6. (A clamp 21 is shown in FIG. 3 to illustrate how the vagina 22 must be opened and held open for insertion of this or any device.) Thus, the longitudinally extending member 20 must be short and slim so as not to cause trauma to the endocervical canal. In one preferred embodiment, the longitudinally extending member 20 has a length of about ½".

Projecting perpendicularly from longitudinally extending member 20 are means for contacting and collecting cells within the endocervical canal. In one presently preferred embodiment of the present invention, the means for contacting and collecting cells within the endocervical canal is a first set of bristles 26 projecting substantially perpendicularly from the longitudinally extending member 20. In FIG. 1, the first set of brushes 26 can be seen projecting from opposing sides of the longitudinally extending member 20. As the first set of bristles 26 are perpendicular to the axis of the longitudinally extending member 20, they are also perpendicular to the axis of the endocervical canal 6 when the longitudinally extending member 20, they are also perpendicular to the axis of the endocervical canal 6 when the longitudinally extended member 20 is inserted, and so provide a mildly abrasive contact with the walls of the endocervical canal which allows sufficient collection of cells. In FIG. 3, the first set of bristles 26 can be seen in contact with the cells of the endocervical canal.

The size of the first set of bristles 26 are preferably of a length sufficient for contacting and collecting cells within the endocervical canal even when the endocervical canal is dilated The desired width of each bristle is such that the bristles are stiff enough to provide abrasive action to obtain a successful sample of cells in the endocervical canal, but sufficiently supple to be somewhat easily compressed when entering an undilated endocervical canal, so as to prevent excess abrasion or damage to the walls.

The spacing between the first set of bristles 26 is preferably such that bristles 26 are spaced closely enough to each other so that collection of the cells from the endocervical canal is possible, yet spaced widely enough from each other so that easy dislodgement of the cells from the first set of bristles 26, when desired, is accommodated. In the preferred embodiment within the scope of the invention, the preferred spacing is about 1/64".

The preferred second bristle means within the scope of the present invention comprises a second member 30 which extends laterally from the flexible zone 18, generally on opposite sides therefrom, from the same point where the longitudinally extending member 20 extends from the flexible zone 18. The laterally extending member 30 is gently curved and is positioned on an axis substantially perpendicular to the axis of the handle 12. As can be seen in FIG. 3, when the device 10 is inserted into the uterus 9, the laterally extending member 30 comes into contact with and rests against the cervical face 8 of the uterus.

In a presently preferred embodiment of the present invention, the laterally extending member 30 is slightly curved so as to conform comfortably to the cervical face, thereby permitting comfortable and full contact between the laterally extending member 30 and the cervical face 8 of the uterus 9. When the laterally extending member 30 is pushed up against the cervical face, the slight curve allows more of the laterally extending member 30 to be in contact with and embrace the cervical face, thereby permitting a greater area of cell collection. It can be appreciated that in older women whose cervices have expanded, embodiments with less of a curve may be preferred.

The laterally extending member 30 also acts as a mechanical barrier against excessive penetration of the endocervical canal by the longitudinally extending member 20. When the laterally extending member 30 rests against the endocervical face 8, further penetration into the endocervical canal 6 by the longitudinally extending member 20 is prohibited. The laterally extending member 30 also provides a means for maintaining an axial relationship between the device 10 and the endocervical canal 6 by guiding placement of the device against the cervical face. Without this axial stability, the longitudinally extending member 20 could be inserted in a misaligned direction and damage to the walls of the endocervical canal may result.

Projecting from the laterally extending member 30 are a second set of bristles for contacting and collecting cells of the cervical face 8. In FIGS. 1 and 3, this second set of bristles 32 can be seen as projecting forwardly from said laterally extending member 30. The second set of bristles preferably has a length whereby they contact the cervical face 8 with enough abrasive action to collect cells, yet with enough softness so as not to cause damage. In one preferred embodiment, the length of each bristle of the second set of bristles is 3/32".

It is important to note that the spacing of the second set of bristles 32 is important in the same way as described above for the first set of bristles 26.

When the second set of bristles 32 are pushed up against the cervical face, they are preferably pushed with sufficient forward pressure to flex them slightly. At this point, the longitudinally extending member 20 is within the endocervical canal. The device 10 is then rotated 360 degrees. With this action, the first set of bristles 26 within the endocervical canal 6 and the second set of bristles 8 against the cervical face 8 rotate and collect cells on their leading edges. Collection of the endocervical cells and the cervical face cells is done simultaneously, and with a successful yield of cells. This is an improvement over the prior art devices which could not consistently, safely, and successfully simultaneously collect endocervical and cervical face cells. As the process itself tends to be embarrassing and somewhat uncomfortable, a high yield of cells from only one try is important, since patients may not be willing to come back to redo an unsuccessful test.

Figure 1A:
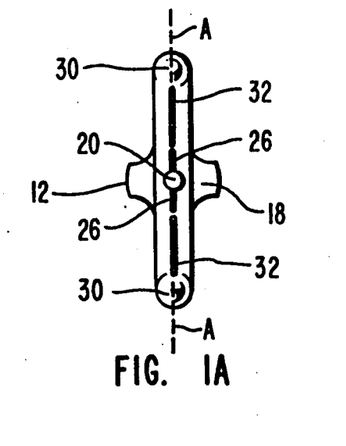
FIG. 1a is an end view of the embodiment of FIG. 1 illustrating single plane positioning of bristles along axis line A—A.

It is another feature in the preferred embodiment of the device of the present invention to have the longitudinally extending member, the laterally extending member, the first and second sets of bristles, and the handle of the device all positioned in the same plane. This feature is best illustrated in FIG. 1a, wherein the first and second set of bristles can be seen to lie in the same plane along axis line A-4. With this embodiment, the cost of manufacture is low due to the fact that molding can more easily be done with a single planed object than with an object with several other dimensions. This low cost of manufacture encourages widespread use of the invention.

Additionally, having the longitudinal 20 and lateral 30 members in the same plane as the set of bristles 32, 26 enhances the removal of cells onto a flat surface. With all parts in one plane, one quick swipe of both sides of the device onto the slide (as pictured in FIG. 4 and later discussed) is all that is necessary.

Further, with all parts in one plane there is less chance of causing excess abrasion and damage to the cervix, while at the same time, there is still successful collection of cells from both the endocervical canal and the cervical face.

It can be appreciated that having the members, the handle, and the bristles in separate planes is also within the scope of the present invention, but it is preferred that they all lie within the same plane.

Figure 4:
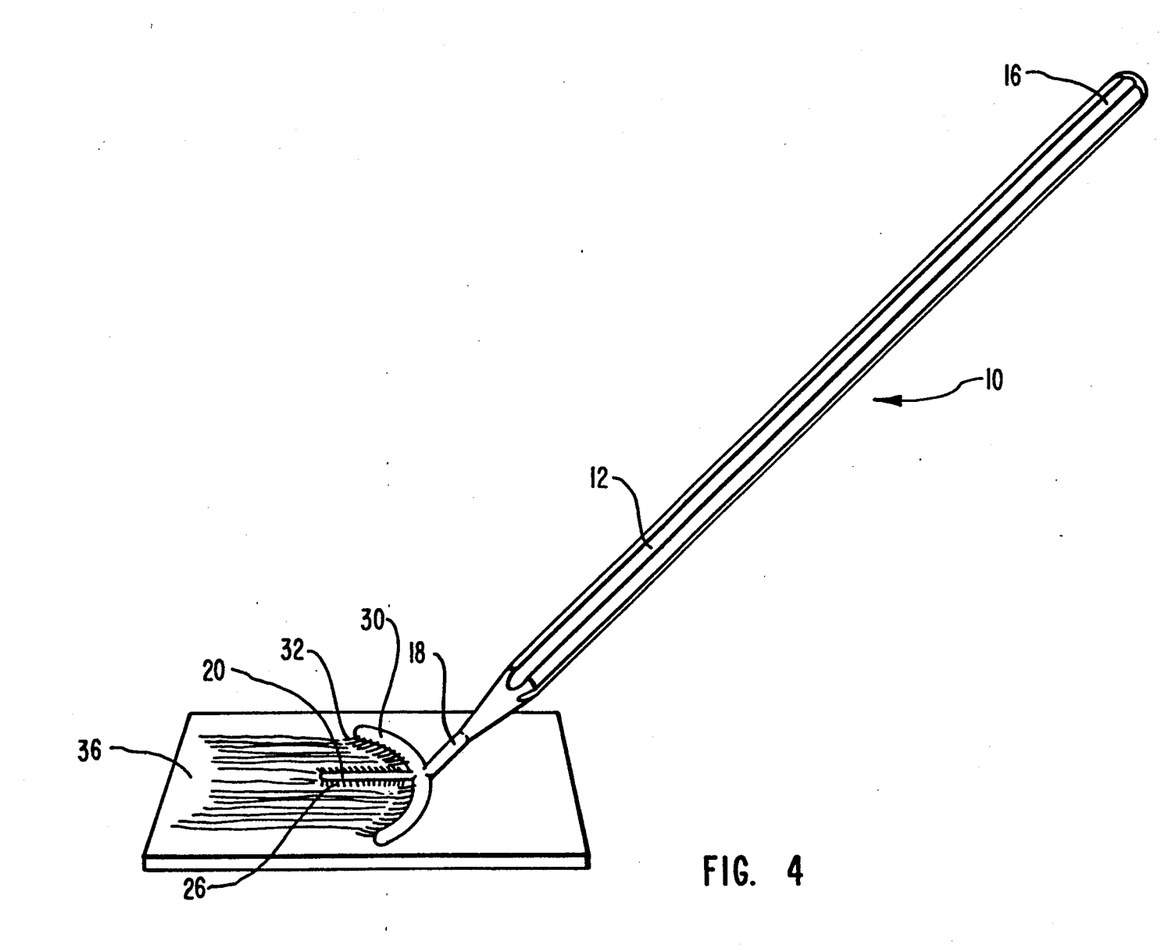
FIG. 4 is a perspective view of cells being transferred from the device of the present invention onto a microscope slide.

Referring now to FIG. 4, one method of removing the cells from the device 10 can be seen. When the device 10 is removed from the uterus, the device 10 contains endocervical and cervical face cells on the leading edges of the sets of bristles Because of the 360 degree rotation, the cervical cells have basically collected only on the leading edges.

One method of removing the cells from the device 10 is to smear the cells onto a microscope slide 36, as can be seen in FIG. 4. The longitudinally extending member 20 and the laterally extending member 30 are placed on the slide 36. The handle 12 is then bent upwards at the flexible zone 18, so that an angle between the handle 12 and the members 20 and 32 is formed while the members 20 and 32 are held parallel to the slide. The user of the device can now easily wipe the cells off of the device onto the slide in a parallel motion. A first smear is made by wiping the device 10 onto the slide 36. The device 10 is then rotated 180 degrees and wiped a second time onto the slide 36. By these two actions, the cells on the leading edges of each side of the bristles are wiped off the device and onto the slide. After a fixative is applied to the slide, the slide is ready for analysis.

It is important to note that without the flexible zone 18, it is awkward to remove the cells from the device onto a slide. There is less maneuverability because, without the flexible zone, the collecting portion cannot be smeared against the slide easily in a parallel motion, and so many of the cells are not transferred to the slide. In contrast, with the flexible zone 18, the longitudinally and laterally extending members 26 and 32 are allowed to be placed flat against the slide 36 and to be maneuvered along the slide by the handle from a position above the slide and pressing downwards, rather than from an awkward position beside the slide, pressing with a sideways motion. Thus, the presence of the flexible zone 18 facilitates removal of cells from the device 10 with a minimum of cell material loss.

Figure 5:
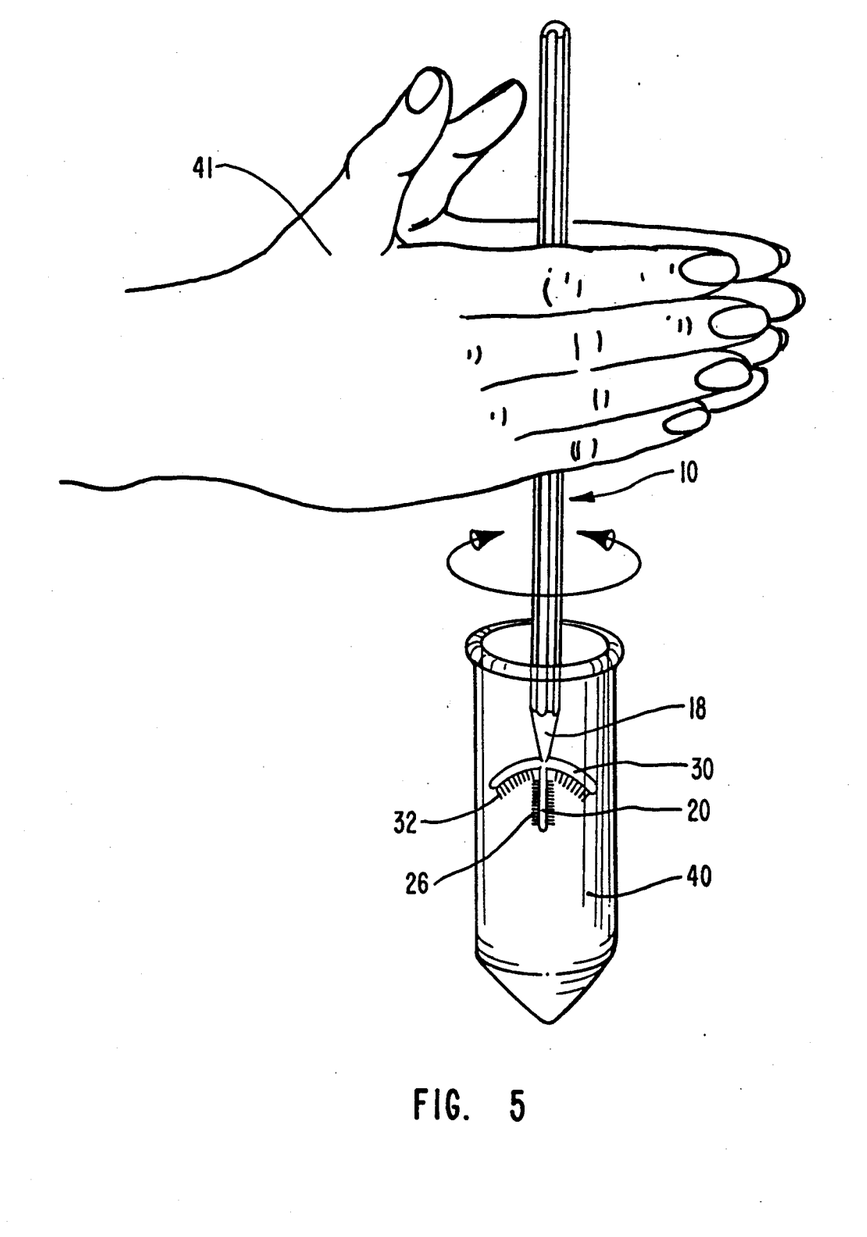
FIG. 5 is a perspective view of cells being transferred from the device of the present invention into a centrifuge tube.

The above-mentioned removal method illustrated in FIG. 4 may result in several layers of cells being stacked on the slide. As any malignant cells may be hidden at the bottom of the stack, this method may not always be sufficient. Thus, an alternative method may be used to create a monolayer preparation in which the cells are applied to the slide in a single layer. Such a method is also facilitated by the device of the present invention and is illustrated in FIG. 5.

By this method, the longitudinally and laterally extending members 26 and 32 are held in a fixative solution in a centrifuge tube 40. The handle 12 is placed between the hands 41 of the user and a rubbing action between the two hands spins the device. Because of the design of the laterally extending member 30, i.e., because it is generally perpendicular to the handle, an oscillating turbulence similar to that found in a washing machine is created by the spinning action. This action releases the cells from the bristles of the device into the fixative solution. The action also dissolves any collected mucous into suspension.

The cells are then spun by a centrifuge into a cell pellet. When this cell pellet is spread onto a slide, a smooth layer, one cell deep, results. Additionally, the cells retrieved for analysis are from both the endocervical canal and the cervical face. As stated earlier, with the prior art devices, many times only one type of cell or the other can be retrieved from the body and tested.

Figure 6:
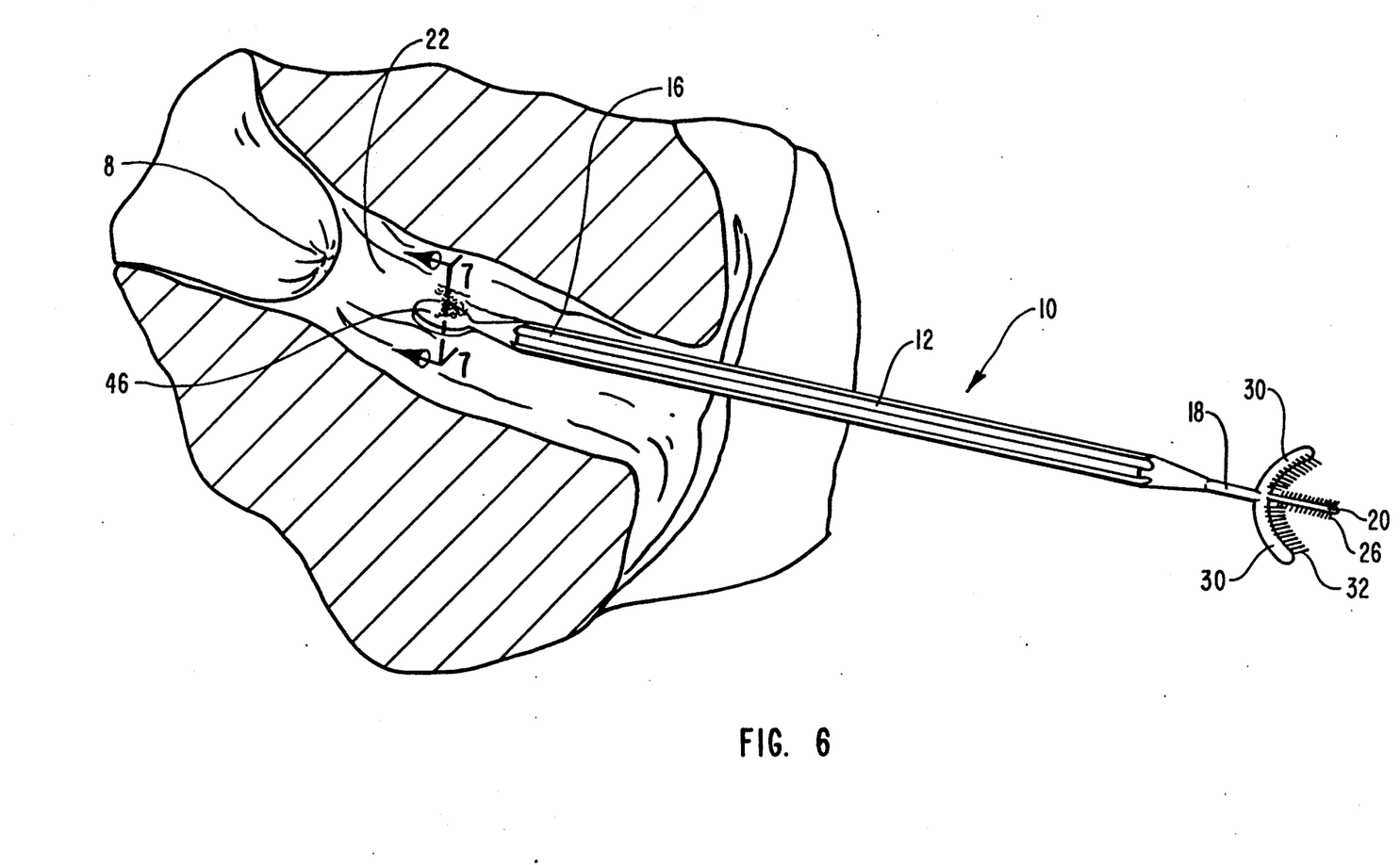
FIG. 6 is a perspective view of a presently preferred embodiment of the present invention illustrating collection of cells from the vaginal wall.

Another important advantage of the device of the present invention is the capability and means for scraping and collecting cells from the vagina 22 located on the same device that simultaneously collects both the endocervical and ectocervical cells. The present invention can also accomplish this as illustrated by the embodiment shown in FIGS. 6 and 7.

In this embodiment, the rear end 16 comprises a spatula-shaped member 46 positioned along the same axis as the axis of the handle 12. The edges 48 of the spatula-shaped member 46 are perpendicular to the faces 50 of the spatula-shaped member 46. This perpendicular shape forms a scraping surface which enables successful yet non-abrasive scraping of the vaginal wall 45 and collection of the vaginal cells. The scraping action of perpendicular edges 48 can be clearly seen in the cross-section of FIG. 7.

Figures 7, 8, 9:
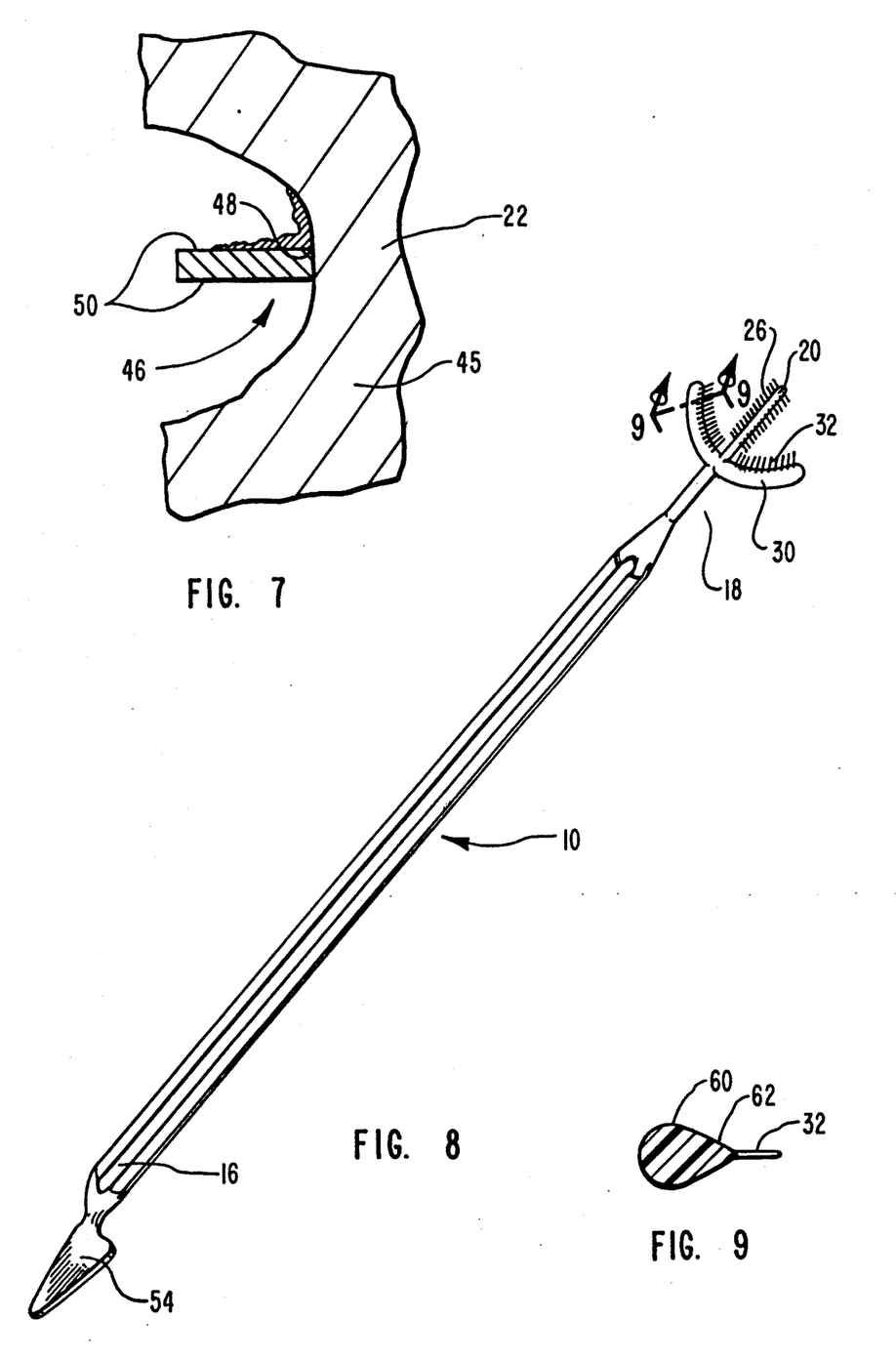
FIG. 7 is a cross-section taken along the line 7—7 of FIG. 6 illustrating the scraping action of the device of the present invention.
FIG. 8 is a perspective view of one alternate embodiment of the device of the present invention.
FIG. 9 is a cross-section of an alternate embodiment taken in the general area long the line 9—9 of FIG. 8.

Another embodiment of the device 10 of the present invention which allows collection of vaginal cells is illustrated in FIG. 8. In this embodiment, a triangular shaped spatula 54 is positioned off the axis of the handle 12 Again, as with the spatula-shaped member 46, the edges of triangular-shaped spatula 54 are perpendicular. By having the triangular-shaped spatula 54 off-axis, maneuverability of the device 10 is increased and collection of vaginal cells is facilitated.

Yet another feature of an alternate embodiment of device 10 can be seen in FIG. 9. In FIG. 9, a cross-section of the laterally extending member 60 is illustrated. In this embodiment, the laterally extending member 60 is tapered to form a narrow forward edge 62 from which the second set of bristles 32 extends.

This particular embodiment facilitates transfer of cells from the laterally extending member 60 to the examination surface by allowing easier access to the second set of laterally extending member. Thus, when the device is wiped along an examination surface such as a slide in a parallel motion, more cells can be available for transfer from the device to the slide for analysis.

In the presently preferred embodiment of the device, the preferred materials from which the device is made are high density polyethylene materials. It will be appreciated that a variety of other materials may also be used. The advantages, however, of using high density polyethylene for manufacture of the present invention are many. First, the handle may be made to be rigid, but when the diameter of the handle is reduced, it can be made to be relatively flexible, so as to bend in the way illustrated in FIG. 4.

The properties of the bristles can also be controlled. With polyethylene, the bristles can be made of a length and width which would be stiff enough to cause sufficient abrasion for collection of cells, yet supple enough to not cause trauma to the cervix. High density polyethylene is also a material which can be molded into the tiny bristles that are used within the scope of the present invention.

Additionally, high density polyethylene is relatively inexpensive. Wire, as used in many art devices, can be about twice as expensive as polyethylene and so cannot be used in such a widespread manner in low cost environments.

From the foregoing, it will be appreciated that a substantial advantage of the device of the present invention that cells from the endocervical canal of the uterus, cells from the cervical face, and cells from the vagina can be collected by the same device. More importantly, cells from the endocervical canal and from the cervical face can be collected simultaneously, without excess abrasion to the uterus, and with successful sampling results.

Additionally, because of the perpendicular configuration of the laterally extending member allowing placement of the member against the cervical face, trauma to the endocervical canal by excessive or misaligned entry by the device into the canal is prevented. Further, the device is axially stabilized. Further yet, the cost of manufacture and use of the device is very low, making the device desirable for widespread use.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A device for collection of tissue cells from a cervical face and endocervical canal of a uterus comprising:
   (a) an elongated handle having a forward end and a rear end;
   (b) tissue sampling means, located at the forward end of said handle, for simultaneously collecting tissue cells from the cervical face and endocervical canal, said sampling means comprising:
      (i) first means providing a plurality of bristles oriented in a row and in a plane for contacting and collecting cells within the endocervical canal as said handle is rotated, said first means aligned with said handle and extending from said forward end therefrom; and
      (ii) second means providing a plurality of bristles oriented in a row and in the same said plane for contacting and collecting cells from the cervical face as said handle is rotated, said second means extending from said forward end of said handle in a direction generally orthogonal to said first means; and
   (c) flexible means positioned at said forward end of said handle for bending said tissue sampling means at an acute angle with respect to the handle for assistance in dislodging the collected tissue cells from said first and second means onto an area for examination.

2. A device as defined in claim 1, wherein said first means comprises:
   (a) a member longitudinally extending from said flexible means at said forward end of said handle; and
   (b) a first set of bristles extending substantially perpendicularly from said longitudinally extending member from the opposing sides thereof.

3. A device as defined in claim 2, wherein the bristles of said first set of bristles have a length such that the overall length of said first set of bristles extending from the opposing sides of said longitudinally extending member is sufficient to contact the endocervical canal, even when the endocervical canal is dilated, and have a width such that said first set of bristles are stiff enough to provide abrasive action yet supple enough to be easily compressed when entering an undilated endocervical canal.

4. A device as defined in claim 2, wherein said second means comprises:

(a) a member laterally extending from said flexible means generally on opposite sides of said flexible means, at a point where said first means extends from said flexible means, said laterally extending member positioned along an axis substantially perpendicular to the axis of said handle, and said laterally extending member having a forward edge which faces said forward end of said handle; and (b) a second set of bristles extending substantially perpendicularly from said laterally extending member along the forward edge thereof for contacting and collecting cells of the cervical face.

5. A device as defined in claim 4, wherein the bristles of said second set of bristles are formed from a material and have a length and width such that said bristles are soft enough to contact the cervical face without causing damage to the cervical face as the second set of bristles is pressed against the cervical face, yet stiff enough to cause enough abrasive action necessary to collect cells.

6. A device as defined in claim 4, wherein said laterally extending member is curved so as generally to conform to the cervical face.

7. A device as defined in claim 4, wherein said forward edge of said laterally extending member is tapered to form a narrow forward edge from which said second set of bristles extends.

8. A device as defined in claim 1, wherein said rear end comprises a means for scraping and collecting cells from the vagina.

9. A device as defined in claim 8, wherein said means for scraping and collecting cells comprises a spatula-shaped member positioned along the same axis as the axis of said handle, said spatula-shaped member having perpendicular edges to enhance collection of cells from the vagina.

10. A device as defined in claim 8, wherein said means for scraping and collecting cells is positioned at an angle relative to the longitudinal axis of said handle.

11. A device as defined in claim 1, wherein said handle is comprised of longitudinally extending ridges.

12. A device for collection of tissue cells from cervical face and endocervical canal of a uterus comprising:
(a) an elongated handle having a forward end and a rear end; and
(b) tissue sampling means, located at the forward end of said handle, for simultaneously collecting tissue cells from the cerivical face and endocervical canal, said sampling means comprising:
(i) first means providing a plurality of bristles oriented in a row and in a plane for contacting the collecting cells within the endocervical canal as said handle is rotated, said first means aligned with said handle and extending from said forward end thereof; and
(ii) second means providing a plurality of bristles oriented in a row and in the same said plane for contacting and collecting cells from the cervical face as said handle is rotated, said second means extending from said forward end of said handle in a direction generally orthogonal to said first means, and said second means comprising means for conforming to said cervical face and maintaining said first means generally in alignment in said endocervical canal when said first means is inserted therein and when said handle is rotated.

13. A device as defined in claim 12, wherein said first means comprises:

(a) a member longitudinally extending from said forward end of said handle; and
(b) a first set of bristles extending substantially perpendicularly from said longitudinally extending member on opposing sides thereof.

14. A device as defined in claim 13, wherein the bristles of said first set of bristles have a length such that the overall length of said first set of bristles extending from the opposing sides of said longitudinally extending member is sufficient to contact the endocervical canal, even when the endocervical canal is dilated, and have a width such that said first set of bristles are stiff enough to provide abrasive action yet supple enough to be easily compressed when entering an undilated endocervical canal.

15. A device as defined in claim 12, wherein said second means comprises:
(a) a member laterally extending from said forward end of said handle at a point where said first means extends from said forward end of said handle, and along an axis substantially perpendicular to the axis of said handle, said laterally extending member having a forward edge which faces said forward end of said handle; and
(b) a second set of bristles extending substantially perpendicularly from said laterally extending member along the forward edge thereof.

16. A device as defined in claim 15, wherein the bristles of said second set of bristles are formed from a material and have a length and width such that said bristles will be soft enough to contact the cervical face without causing damage to the cervical face as the second set of bristles is pressed against the cervical face, yet stiff enough to cause enough abrasive action necessary to collect cells.

17. A device as defined in claim 15, wherein said laterally extending member is curved so as generally to conform to the cervical face.

18. A device as defined in claim 15, wherein said forward edge of said laterally extending member is tapered to form a narrow forward edge from which said second set of bristles extends.

19. A device as defined in claim 12, wherein said rear end comprises a means for scraping and collecting cells from the vagina.

20. A device as defined in claim 19, wherein said means for scraping and collecting cells comprises an spatula-shaped member positioned along the same axis as the axis of said handle, said spatula-shaped member having perpendicular edges to enhance collection of cells from the vagina.

21. A device as defined in claim 20, wherein said means for scraping and collecting cells is positioned at an angle relative to the longitudinal axis of said handle.

22. A device as defined in claim 12, wherein said handle is comprised of longitudinally extending ridges.

23. A device as defined in claim 12, wherein said forward end of said handle narrows into a flexible zone.

24. A device for collection of tissue cells from a cervical face and endocervical canal of a uterus comprising:
(a) an elongated handle having a forward end and a rear end; and
(b) tissue sampling means, located at the forward end of said handle, for simultaneously collecting tissue cells from the cervical face and endocervical canal, said sampling means comprising:
(i) first means providing a plurality of bristles oriented in a row and in a plane for contacting and collecting cells within the endocervical canal as said handle is rotated, said first means aligned with said handle and extending from said forward end thereof; and (ii) second means providing a plurality of bristles oriented in a row and in the same said plane for contacting and collecting cells from the cervical face as said handle is rotated, and said second means extending from said forward end of said handle in a direction generally orthogonal to said first means.

25. A device as defined in claim 24, wherein said first means comprises:

(a) a member longitudinally extending from said forward end of said handle; and (b) a first set of bristles extending substantially perpendicularly from said longitudinally extending member on opposing sides thereof.

26. A device as defined in claim 25, wherein the bristles of said first set of bristles have a length such that the overall length of said first set of bristles extending from the opposing sides of said longitudinally extending member is sufficient to contact the endocervical canal, even when the endocervical canal is dilated, and have a width such that said first set of bristles are stiff enough to provide abrasive action yet supple enough to be easily compressed when entering an undilated endocervical canal.

27. A device as defined in claim 24, wherein said second means comprises:

(a) a member laterally extending from said forward end of said handle at a point where said first means extends from said forward end of said handle, and along an axis substantially perpendicular to the axis of said handle, said laterally extending member having a forward edge which faces said forward end of said handle; and (b) a second set of bristles extending substantially perpendicularly from said laterally extending member along the forward edge thereof.

28. A device as defined in claim 27, wherein the bristles of said second set of bristles are formed from a material and have a length and width such that said bristles will be soft enough to contact the cervical face without causing damage to the cervical face as the second set of bristles is pressed against the cervical face, yet stiff enough to cause enough abrasive action necessary to collect cells.

29. A device as defined in claim 27, wherein said laterally extending member is curved so as generally to conform to the cervical face.

30. A device as defined in claim 27, wherein said forward edge of said laterally extending member is tapered to form a narrow forward edge from which said second set of bristles extends.

31. A device as defined in claim 24, wherein said rear end comprises a means for scraping and collecting cells from the vagina.

32. A device as defined in claim 31, wherein said means for scraping and collecting cells comprises a spatula-shaped member positioned along the same axis as the axis of said handle, said spatula-shaped member having perpendicular edges to enhance collection of cells from the vagina.

33. A device as defined in claim 31, wherein said means for scraping and collecting cells is positioned at an angle from the axis of said handle.

34. A device as defined in claim 24, wherein said handle is comprised of longitudinally extending ridges.

35. A device as defined in claim 24, wherein said forward end of said elongated handle narrows into a flexible zone.

36. A device for collection of tissue cells from a cervical face and endocervical canal of a uterus comprising:

(a) an elongated handle having a forward end and a rear end, said forward end narrowing into a flexible zone of said handle;

(b) a member longitudinally extending from said flexible zone along the same axis as said handle, said longitudinally extending member having a length for insertion into the endocervical canal;

(c) a first set of bristles for contacting and collecting cells within the endocervical canal, said first set of bristles projecting substantially perpendicularly from said longitudinally extending member and being oriented in a plane;

(d) a member laterally extending from said flexible zone generally on opposite sides of said handle, at the point where said longitudinally extending member extends from said flexible zone, said laterally extending member positioned along an axis generally orthogonal to the axis of said handle and having a forward edge which faces said forward end of said handle, said laterally extending member being curved so as to generally conform to the cervical face, and said laterally extending member comprising means for maintaining said longitudinally extending member generally in alignment in said endocervical canal when said longitudinally extending member is inserted therein and when said handle is rotated;

(e) a second set of bristles for contacting and collecting cells on the cervical face of the uterus, said second set of bristles projecting from said forward edge of said laterally extending member along the same plane as said first set of bristles, and said second set of bristles being formed of a material and having a length and width such that said second set of bristles are soft enough to contact the cervical face without causing damage to the cervical face as the second set of bristles are pressed against the cervical face, yet stiff enough to cause enough abrasive action necessary to collect cells.

* * * * *